(12) United States Patent
Wang et al.

(10) Patent No.: US 8,810,781 B2
(45) Date of Patent: Aug. 19, 2014

(54) DEVICE AND METHOD FOR MEASURING VAPORIZATION-MELT RATIO

(76) Inventors: Xuyue Wang, Dalian (CN); Lianji Wang, Dalian (CN); Wenji Xu, Dalian (CN); Yande Liang, Dalian (CN); Renke Kang, Dalian (CN); Dongming Guo, Dalian (CN)

( * ) Notice: Subject to any disclaimer, the term of this patent is extended or adjusted under 35 U.S.C. 154(b) by 0 days.

(21) Appl. No.: 13/447,314

(22) Filed: Apr. 16, 2012

(65) Prior Publication Data
US 2012/0200848 A1 Aug. 9, 2012

Related U.S. Application Data

(63) Continuation-in-part of application No. PCT/CN2010/077693, filed on Oct. 13, 2010.

(30) Foreign Application Priority Data

Oct. 15, 2009 (CN) .......................... 2009 1 0308292

(51) Int. Cl.
*G01N 21/00* (2006.01)
*G02B 27/54* (2006.01)
*G01N 5/04* (2006.01)

(52) U.S. Cl.
CPC . *G02B 27/54* (2013.01); *G01N 5/04* (2013.01)
USPC ............................................ 356/73; 356/416

(58) Field of Classification Search
USPC .............................. 356/72–73, 416, 436–437
See application file for complete search history.

(56) References Cited

U.S. PATENT DOCUMENTS

| | | | | |
|---|---|---|---|---|
| 2,547,212 A | * | 4/1951 | Jamison et al. ................ | 356/410 |
| 3,600,590 A | * | 8/1971 | Einstein ......................... | 356/439 |
| 3,995,960 A | * | 12/1976 | Fletcher et al. ............... | 356/433 |
| 5,163,332 A | * | 11/1992 | Wong ............................. | 356/437 |
| 5,178,744 A | * | 1/1993 | Nakazawa et al. ............ | 204/425 |
| 5,834,777 A | * | 11/1998 | Wong ............................. | 250/343 |
| 5,936,250 A | * | 8/1999 | Baliga et al. .................. | 250/345 |

* cited by examiner

*Primary Examiner* — Kara E Geisel
(74) *Attorney, Agent, or Firm* — Matthias Scholl P.C.; Matthias Scholl

(57) ABSTRACT

A detection device is described for measuring the vaporization-melt ratio, the device including a light source, a first and second optical lens group, a slit, a first and second steering mirror, a first and second primary mirror, a glass container, a colored blade, and a high-speed recording analyzer. The first primary mirror and the second primary mirror are symmetrically placed at both ends of the glass container. The first optical lens group is located between the light source and the slit. The second optical lens group is located between the colored blade and the high-speed recording analyzer. The first steering mirror is installed behind the slit, passing the light from the slit to the first primary mirror. The light reflected by the second primary mirror is passed to the colored blade from the second steering mirror located between the second primary mirror and the colored blade.

2 Claims, 1 Drawing Sheet

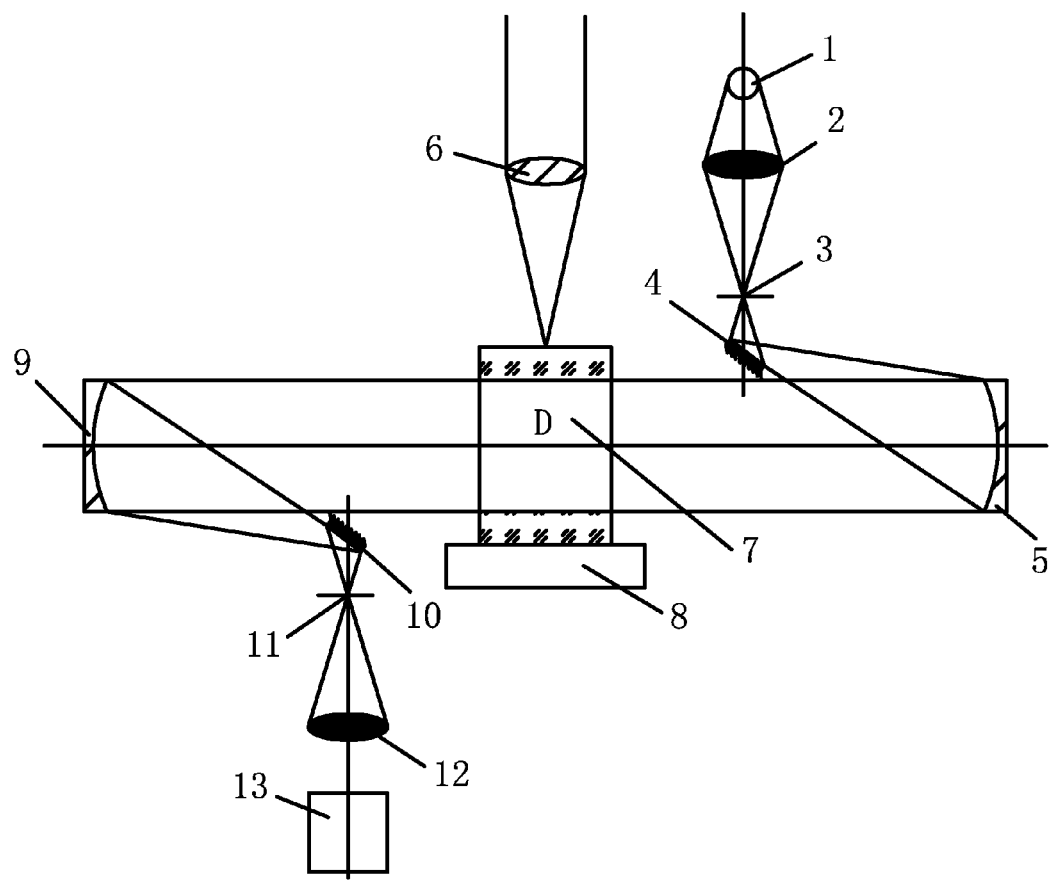

DEVICE AND METHOD FOR MEASURING VAPORIZATION-MELT RATIO

CROSS-REFERENCE TO RELATED APPLICATIONS

This application is a continuation-in-part of International Patent Application No. PCT/CN2010/077693 with an international filing date of Oct. 13, 2010, designating the United States, now pending, and further claims priority benefits to Chinese Patent Application No. 200910308292.4 filed Oct. 15, 2009. The contents of all of the aforementioned applications, including any intervening amendments thereto, are incorporated herein by reference.

BACKGROUND OF THE INVENTION

1. Field of the Invention

The invention relates to the field of precision machining technology, and specifically to a device and method for measuring the vaporization-melt ratio in laser processing.

2. Description of the Related Art

The dimensions of the outlines of high-performance slit array antenna panels made of aluminum alloy in aerospace aircraft radar, missile antennae, and ship navigation systems range from 100-600 mm, while the thickness thereof is only 0.3-0.4 mm. This requires processing many rectangular narrow slits in different directions to form a slit array, with a gap width of 0.1-0.3 mm. Dimensional and shape accuracy are required to be 0.1-1 μm, and machined surface quality must be Ra<1.6 μm, with zero microscopic burrs or flash. Similarly, the stainless steel high-density porous filter plates used in the petroleum and chemical industries for fluid purification have sizes ranging from 80-200 mm and thicknesses from 0.5-2 mm. Furthermore, a large number of microscopic and high-density distributions of pores are required to be produced on the filter plates, and the shape of the pores can be circular, rectangular or even profiled. The diameters of the pores are 0.1-0.3 mm, limited by the ratio of depth to diameter, which in turn restrict the design thickness. Regarding the carbide nozzles of the spinneret, dusting and inkjet used in the textile industry, light industry, printing industry, and other industries, the dimension of the outline of the carbide nozzles is 10-100 mm, the pore size is 0.1-0.3 mm, and nozzle wall thickness is 0.1-0.3 mm. In addition, it is urgent to develop an efficient, high-quality, and precise machining method for preparation of a medical micro fluidic chip and a mold of the stainless steel micro-flow channel of the chip.

The structure of the above-mentioned precision panels is characterized by a fine structure of holes, complex and differing shapes, dense and small slit size, and thin-walled structure. Also, the above-mentioned precision panels are characterized by the larger ratio between their outline size and their thickness. High accuracy in machining, shape accuracy, and surface quality are required. The special alloy employed and other metal with high thermal conductivity cause mechanical and thermal deformation of thin-walled precision sheet metal parts during processing. Limited by tool size, the cutting performance of small holes and seam processing is relatively poor. Traditional processing methods have difficulty meeting the requirements of high precision, high quality, and high efficiency.

Because of the direct impact of vaporization-melt ratio on precision and quality in laser machining, it is of both theoretical and practical importance to research and develop an apparatus and method of vaporization-melt ratio detection in laser processing.

SUMMARY OF THE INVENTION

The invention aims to solve the technical problems of processing a high-performance slit array antenna panel made of aluminum alloy in the fields of aerospace vehicles radar, missile antennae, and ship navigation systems. The weight of material removed during gasification is calculated by identifying the form of removal vapors, collecting flow data, considering the refractive index change and distribution characteristics based on the relationship between the refractive index and density in the transmission of the beam, and quantitatively analyzing the form of gasification at different times. The weight of the sample and molten removal is accurately determined before and after processing to determine the weight of vapors and the molten removal. It is necessary to investigate the influence of laser energy input on the vaporization-melt ratio, further developing the experimental and theoretical basis for the impact of the vaporization-melt ratio on processing size, accuracy, and surface quality.

Light is passed through the slit, a steering mirror, and a primary mirror of optical lens group, and radiates on an object D placed in a transparent and breathable glass container. The information of the vapors is transmitted to the high-speed recording analyzer from the primary mirror, the steering mirror, and through a colored blade. The vaporization-melt ratio is calculated by analyzing the information of the vapors at different moments, assisted by precision weighing.

To achieve the above objective, in accordance with one embodiment of the invention, there is provided a device for measuring vaporization-melt ratio in laser processing, the device comprising a light source, a first optical lens group and a second optical lens group, a slit, a first steering mirror and a second steering mirror, a first primary mirror and a second primary mirror, a glass containers, an electronic weighing instrument, a colored blade, and a high-speed recording analyzer. The first primary mirror and the second primary mirror are symmetrically placed at both ends of the glass container. The first optical lens group is located between the light source and the slit. The second optical lens group is located between the colored blade and the high-speed recording analyzer. The first steering mirror is installed behind the slit, passing the light from the slit to the first primary mirror. The light reflected by the second primary mirror is passed to the colored blade from the second steering mirror, which is located between the second primary mirror and the colored blade. The light source is a krypton lamp, from which the light is passed to the slit by the first optical lens group. The light is passed to the first primary mirror by the first steering mirror. The beam from the light source is directed by the first primary mirror onto an object D in the glass container. The beam is reflected by the second steering mirror to the second primary mirror and then through the colored blade to the high-speed recording analyzer. Finally, the vaporization-melt ratio of the processing vapors is calculated by analyzing the reflected beam by the high-speed recording analyzer at different moments.

A method for measuring the vaporization-melt ratio in laser processing using the detection device comprises the steps of:

1) generating vapors in the laser processing; based on the optical schlieren measurement principle of vapors, detecting the refractive index change after the light passes through the vapors, identifying the form of vapors and density variations, calculating the density distribution of gasification in different moments according to the Gladstone-Dale gaseous equation to obtain the weight of the vapors at different times; and 2) accurately measuring the weight of the work piece before and after complete laser processing using a higher-resolution weighing method; carefully collecting and weighing molten isolates in the glass container to obtain the weight of the vapors, the molten isolates and the vaporization-melt ratio; for homogeneous materials, excluding the weight of particles stripped directly away from the substrate, and measuring the vaporization-melt ratio; for uneven materials, collecting the particles stripped from the substrate and weighing them, to eliminate the effect of the weight of the stripped particles, whereby amending the vaporization-melt ratio; for melting recasts, detecting the volume of recast layer based on image processing to eliminate the effects on the weight of material removal by metallographic analysis, whereby a precise vaporization-melt ratio is obtained.

Advantages of the invention include using the vaporization-melt ratio detection device and method to effectively grasp the interactive status and conditions between laser and material, and to meet the requirement of high-quality removal of processing products through analysis and control of the ratio between vapors and melts in the processing zone. This is an effective way to process the microscopic structures to improve precision and quality during laser forming and manufacturing for surpassing the original processing equipment and quality indicators. Processing a variety of cavity materials and structural parts, such as 0.05-0.2 mm sized holes with depth-to-diameter ratio of 20:1 solves technical problems of filter structure in the fields of radar antenna panels in the textile, petroleum, and chemical industries. Meeting the technical requirements of micro-structural parts requires improving the precision and quality of laser processing by an order of magnitude to solve processing problems of the microscopic plastic mold groove cavity, including size, shape, position accuracy and quality requirements.

BRIEF DESCRIPTION OF THE DRAWINGS

The invention is described hereinbelow with reference to accompanying drawings, in which the sole FIGURE is a schematic diagram of a detection device of vaporization-melt ratio in laser processing in accordance with one embodiment of the invention.

In the drawings, the following reference numbers are used: 1. light source; 2. first optical lens group; 3. slit; 4. first steering mirror; 5. first primary mirror; 6. laser head; 7. glass container; 8. electronic weighing instrument; 9. second primary mirror; D. object; 10. second steering mirror; 11. colored blade; 12. second optical lens group; 13. high-speed recording analyzer.

DETAILED DESCRIPTION OF THE EMBODIMENTS

For further illustrating the invention, experiments detailing a device and method for measuring the vaporization-melt ratio in laser processing are described below. It should be noted that the following examples are intended to describe and not to limit the invention.

As shown in the FIGURE, a detection device for vaporization-melt ratio in laser processing comprises a light source 1, a first optical lens group 2 and a second optical lens group 12, a slit 3, a first steering mirror 4 and a second steering mirror 10, a first primary mirror 5 and a second primary mirror 9, a glass container 7, an electronic weighing instrument 8, an object D, a colored blade 11, and a high-speed recording analyzer 13. The first primary mirror and the second primary mirror are symmetrically placed at both ends of the glass container. The first optical lens group 2 is located between the light source 1 and the slit 3. The second optical lens group 12 is located between the colored blade 11 and the high-speed recording analyzer 13. The first steering mirror 4 is installed behind the slit 3, passing the light through the slit 3 to the first primary mirror 5. The light reflected by the second primary mirror 9 is passed to the colored blade 11 through the second steering mirror 10 located between the second primary mirror 9 and the colored blade 11. The light source 1 is a krypton lamp, from which the light is passed to the slit 3 by the first optical lens group 2. The light is passed to the first primary mirror 5 by the first steering mirror 4. The beam from the light source 1 is directed by the first primary mirror 5 onto the object D in the glass container 7. The beam is then reflected by the second steering mirror 10 to the second primary mirror 9 and then through the colored blade 11 to the high-speed recording analyzer 13. Finally, the vaporization-melt ratio is calculated by analyzing the reflected beam by the high-speed recording analyzer at different moments.

The detection device is placed on a laser processing machine. A laser beam from the laser head 6 through the upper window radiates on the object D in the glass container 7. Meanwhile, the processing vapors are radiated by the detection light from the light source 1 passing through the right window of the glass container 7. The status information of vapors is passed out from the left window of the glass container 7 through the second primary mirror 9, the second steering mirror 10, and the colored blade 11, finally collected, recorded, and analyzed by a high-speed recording analyzer 13. The glass container 7 as a transparent and breathable device allows vapors to escape at any time. The state of vapors is collected, recorded, and analyzed by the high-speed recording analyzer during the entire process. Detailed implementation is demonstrated as follows.

Laser processing of a 50 g slit array antenna panel is taken as an example. When the vapors are radiated by the detection light, based on the optical schlieren measurement principle of vapors, detecting the refractive index change after the light passes through the vapors, and identifying the form of vapors and density variations, the density distribution of the vapors in different moments is calculated according to the Gladstone-Dale gaseous equation. The weight of vapors is approximately 5 g. At the same time, the weight of the work piece before and after the complete laser processing is accurately weighed to calculate the weight of the vapors. Then, the melts in the glass container 7 are carefully collected and weighed by the electronic weighing instrument 8 to obtain the weight of the melts, finally yielding the vaporization-melt ratio. In this case, the weight of the vapors, that is, the difference between work piece weight before and after laser processing, is about 5 g. On the other hand, the melts are carefully collected and weighed, yielding a figure of 5 g. Thus, total removal is 10 g during processing, while the vaporization-melt ratio is 1. The vaporization-melt ratio is controlled by changing the laser energy input. For example, processing a total removal of 10 g, 8 g for the vapors and 2 g for the melts, the vaporization-melt ratio is 4. Evidently, the processing quality of value 4 is, significantly, an order of magnitude higher than that of value 1. For homogeneous materials, excluding the weight of particles stripped directly away from the substrate, the vaporization-melt ratio is measured via the above method. In comparison, for not homogeneous materials, the particles stripped from the substrate are collected and weighed to eliminate the effect of the weight of the stripped particles. Similarly, it is possible to obtain the weight of the stripped particles and the total weight of material removal by using a precise weighing method. After correction, the accurate ratio between gasification and melting weight is obtained. Finally, by metallographic analysis, the volume of the recast layer is detected based on image processing to eliminate the effects on the weight of material removal, yielding a precise vaporization-melt ratio. This method can be applied to laser cutting, milling, cladding, and other processing of vaporization-melt ratio detection.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for measuring vaporization-melt ratio, comprising:
   a) a light source (1);
   b) a first optical lens group (2);
   c) a second optical lens group (12);
   d) a slit (3);
   e) a first steering mirror (4);
   f) a second steering mirror (10);
   g) a first primary mirror (5);
   h) a second primary mirror (9);
   i) a glass container (7);
   j) a colored blade (11);
   k) a high-speed recording analyzer (13); and
   l) an electronic weighing instrument (8);
wherein:
   the glass container (7) is a transparent and air-permeable container;
   the first primary mirror (5) and the second primary mirror (9) are symmetrically placed at both ends of the glass container (7);
   the first optical lens group (2) is located between the light source (1) and the slit (3);
   the second optical lens group (12) is located between the colored blade (11) and the high-speed recording analyzer (13);
   the first steering mirror (4) is installed behind the slit (3);
   the second steering mirror (10) is located between the second primary mirror (9) and the colored blade (11);
   the light source (1) is a krypton lamp;
   the glass container (7) functions to contain an object;
   the object is laser processed to generate vapors, melts, a recast layer, and a processed object;
   the glass container (7) is disposed above the electronic weighing instrument (8);
   the electronic weighing instrument (8) weighs the glass container (7), a weight of the object, a weight of the melts, and a weight of the processed object; and
   a light from the light source (1) is transmitted through the first optical lens group (2) and the slit (3), the light is reflected by the first steering mirror (4) to the first primary mirror (5), the light is directed by the first primary mirror (5) onto the object, the light is reflected by the second primary mirror (9) to the second steering mirror (10), the light is transmitted through the colored blade (11) and the second optical lens group (12), and the light is finally detected and analyzed by the high-speed recording analyzer (13) to calculate a weight of the vapors and a volume of the recast layer, and to calculate a vaporization-melt ratio of the object by dividing the weight of the vapors by the weight of the melts.

2. A method for measuring vaporization-melt ratio in laser processing using a device, the device comprising:
   a) a light source (1);
   b) a first optical lens group (2);
   c) a second optical lens group (12);
   d) a slit (3);
   e) a first steering mirror (4);
   f) a second steering mirror (10);
   g) a first primary mirror (5);
   h) a second primary mirror (9);
   i) a glass container (7);
   j) a colored blade (11);
   k) a high-speed recording analyzer (13); and
   l) an electronic weighing instrument (8);
wherein:
   the glass container (7) is a transparent and air-permeable container;
   the first primary mirror (5) and the second primary mirror (9) are symmetrically placed at both ends of the glass container (7);
   the first optical lens group (2) is located between the light source (1) and the slit (3);
   the second optical lens group (12) is located between the colored blade (11) and the high-speed recording analyzer (13);
   the first steering mirror (4) is installed behind the slit (3);
   the second steering mirror (10) is located between the second primary mirror (9) and the colored blade (11);
   the light source (1) is a krypton lamp;
   the glass container (7) functions to contain an object;
   the glass container (7) is disposed above the electronic weighing instrument (8);
   the electronic weighing instrument (8) weighs the glass container (7) and the weight of the object; and
   a light from the light source (1) is transmitted through the first optical lens group (2) and the slit (3), the light is reflected by the first steering mirror (4) to the first primary mirror (5), the light is directed by the first primary mirror (5) onto the object, the light is reflected by the second primary mirror (9) to the second steering mirror (10), the light is transmitted through the colored blade (11) and the second optical lens group (12), and the light is finally detected and analyzed by the high-speed recording analyzer (13);
the method comprising the steps of:
   a) placing an object inside the glass container (7) and measuring a weight of the object; laser processing the object and generating vapors, melts, a recast layer, and a processed object; and detecting a refractive index of the vapors after the light passes through the vapors, identifying a form of the vapors and density variations, and calculating a density distribution of the vapors according to a Gladstone-Dale equation;
   b) measuring a weight of the processed object after laser processing the object; when the object is homogeneous, calculating a weight of the vapors by subtracting the weight of the processed object from the weight of the object; or when the object is not homogeneous, collecting particles stripped from the object and measuring a weight of the particles, and calculating a weight of the vapors by subtracting the weight of the processed object and the weight of the particles from the weight of the object;

c) collecting and measuring a weight of the melts in the glass container (7), image processing and metallographic analyzing the recast layer to measure a volume of the recast layer, and modifying the weight of the melts according to the volume of the recast layer; and
d) calculating a vaporization-melt ratio of the object by dividing the weight of the vapors by the weight of the melts.

* * * * *